United States Patent
Haverfield

(10) Patent No.: US 8,371,998 B2
(45) Date of Patent: *Feb. 12, 2013

(54) METHOD OF TREATING ANAL INCONTINENCE

(75) Inventor: Maxwell E. Haverfield, Epping (AU)

(73) Assignee: American Research Corporation, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/891,941

(22) Filed: Sep. 28, 2010

(65) Prior Publication Data

US 2011/0060180 A1  Mar. 10, 2011

Related U.S. Application Data

(63) Continuation of application No. 11/428,090, filed on Jun. 30, 2006, now Pat. No. 7,828,715.

(60) Provisional application No. 60/806,209, filed on Jun. 29, 2006.

(51) Int. Cl.
*A61F 2/02* (2006.01)

(52) U.S. Cl. .......................................... 600/30

(58) Field of Classification Search .............. 600/29–31, 600/37
See application file for complete search history.

(56) References Cited

U.S. PATENT DOCUMENTS

| | | | |
|---|---|---|---|
| 3,943,938 A | 3/1976 | Wexler et al. | |
| 4,153,059 A | 5/1979 | Fravel et al. | |
| 4,231,369 A | 11/1980 | Sorensen et al. | |
| 4,258,705 A | 3/1981 | Sorensen et al. | |
| 4,399,809 A | 8/1983 | Baro et al. | |
| 4,537,195 A | 8/1985 | McDonnell | |
| 4,753,648 A | 6/1988 | Jackson | |
| 4,911,149 A | 3/1990 | Borodulin et al. | |
| 4,979,947 A | 12/1990 | Berman | |
| 5,112,344 A | 5/1992 | Petros | |
| 5,117,840 A | 6/1992 | Brenman et al. | |
| 5,314,458 A | 5/1994 | Najafi et al. | |
| 5,385,577 A | 1/1995 | Maurer et al. | |
| 5,593,443 A | 1/1997 | Carter et al. | |
| 5,611,515 A | 3/1997 | Benderev et al. | |
| 5,769,877 A | 6/1998 | Barreras, Sr. | |
| 5,807,397 A | 9/1998 | Barreras | |
| 5,842,478 A | 12/1998 | Benderev et al. | |
| 5,860,425 A | 1/1999 | Benderev et al. | |
| 5,899,909 A | 5/1999 | Claren et al. | |
| 6,042,534 A | 3/2000 | Gelman | |
| 6,110,101 A | 8/2000 | Tihon et al. | |

(Continued)

FOREIGN PATENT DOCUMENTS

| WO | WO 00/57796 | 10/2000 |
|---|---|---|
| WO | WO 03/092546 | 11/2003 |

(Continued)

OTHER PUBLICATIONS

Dean et al., "Silicone elastomer sling for fecal Incontinence in dogs," Vet Surg, vol. 17, No. 6, pp. 304-310, 1988.

(Continued)

*Primary Examiner* — Charles A Marmor, II
*Assistant Examiner* — Catherine E Burk
(74) *Attorney, Agent, or Firm* — Kagan Binder PLLC

(57) ABSTRACT

A method for treating anal incontinence is provided, in which a support member is implanted in a tissue pathway extending from a first location posterior to and adjacent the anus, through the perineum anterior to the anus and terminating at a location posterior to and adjacent the anus opposite the first location.

13 Claims, 9 Drawing Sheets

U.S. PATENT DOCUMENTS

| | | |
|---|---|---|
| 6,277,392 B1 | 8/2001 | Klein |
| 6,309,686 B1 | 10/2001 | Zietlow et al. |
| 6,350,276 B1 | 2/2002 | Knowlton |
| 6,454,698 B1 | 9/2002 | Forsell |
| 6,461,292 B1 | 10/2002 | Forsell |
| 6,464,628 B1 | 10/2002 | Forsell |
| 6,471,635 B1 | 10/2002 | Forsell |
| 6,482,145 B1 | 11/2002 | Forsell |
| 6,503,189 B1 | 1/2003 | Forsell |
| 6,505,630 B1 | 1/2003 | Sonksen |
| 6,530,933 B1 | 3/2003 | Yeung et al. |
| 6,575,897 B1 | 6/2003 | Ory et al. |
| 6,606,518 B1 | 8/2003 | Cigaina |
| 6,613,031 B2 | 9/2003 | Glasglow et al. |
| 6,626,916 B1 | 9/2003 | Yeung et al. |
| 6,632,210 B1 | 10/2003 | Glasgow et al. |
| 6,635,678 B1 | 10/2003 | Kamm et al. |
| 6,638,208 B1 | 10/2003 | Natarajan et al. |
| 6,716,229 B2 | 4/2004 | Toth |
| 6,749,624 B2 | 6/2004 | Knowlton |
| 6,911,003 B2 | 6/2005 | Anderson et al. |
| 6,981,983 B1 | 1/2006 | Rosenblatt et al. |
| 7,828,715 B2 * | 11/2010 | Haverfield ............ 600/30 |
| 2002/0019579 A1 | 2/2002 | Silverman et al. |
| 2003/0032857 A1 | 2/2003 | Forsell |
| 2003/0045775 A1 | 3/2003 | Forsell |
| 2003/0077244 A1 | 4/2003 | Petersen |
| 2003/0088148 A1 | 5/2003 | Forsell |
| 2003/0092962 A1 | 5/2003 | Forsell |
| 2003/0153806 A1 | 8/2003 | Miller |
| 2003/0220538 A1 | 11/2003 | Jacquetin |
| 2003/0233150 A1 | 12/2003 | Bourne et al. |
| 2004/0006353 A1 | 1/2004 | Bosley, Jr. et al. |
| 2004/0010182 A1 | 1/2004 | Silverman et al. |
| 2004/0034275 A1 | 2/2004 | Forsell |
| 2004/0039453 A1 * | 2/2004 | Anderson et al. ......... 623/23.72 |
| 2004/0055610 A1 | 3/2004 | Forsell |
| 2004/0064030 A1 | 4/2004 | Forsell |
| 2004/0064110 A1 | 4/2004 | Forsell |
| 2004/0138725 A1 | 7/2004 | Forsell |
| 2004/0148021 A1 | 7/2004 | Cartledge et al. |
| 2004/0186515 A1 | 9/2004 | Rosenblatt |
| 2004/0249453 A1 | 12/2004 | Cartledge et al. |
| 2004/0249473 A1 | 12/2004 | Delorme et al. |
| 2004/0250820 A1 | 12/2004 | Forsell |
| 2005/0245787 A1 * | 11/2005 | Cox et al. ............ 600/37 |
| 2005/0283189 A1 | 12/2005 | Rosenblatt |
| 2008/0021265 A1 | 1/2008 | Garbin et al. |

FOREIGN PATENT DOCUMENTS

| | | |
|---|---|---|
| WO | WO 2006/069078 | 6/2006 |

OTHER PUBLICATIONS

McMahan et al., "Rectal prolapse. An update on the rectal sling procedure," Am Surg., vol. 53, No. 1, pp. 37-40, 1987.

Horn et al., "Sphincter repair with a Sliastic sling for anal incontinence and rectal procidentia," Dis Colon Rectum, vol. 28, No. 11, pp. 868-872, 1985.

O'Rourke et al., "A puborectal sling in the management of anal incontinence and rectal prolapse," Aust N Z J Surg., vol. 55, No. 5, pp. 493-495, 1985.

Holschneider, "The use of a levator ani sling in anal Incontinence," An Esp Pediatr., vol. 13, No. 4, pp. 335-338, 1980.

O'Rourke, "An anorectal sling in the treatment of rectal prolapse and incontinence," Aust N Z J Surg., vol. 44, No. 2, pp. 144-146, 1974.

Yamana et al., "Perineal Puborectalis Sling Operation for Fecal Incontinence: Preliminary Report," Diseases of the Colon & Rectum, The American Society of Colon and Rectal Surgeons, vol. 47, No. 11, 2004, 16 pp., 1982-1989.

* cited by examiner

US 8,371,998 B2

METHOD OF TREATING ANAL INCONTINENCE

CROSS-REFERENCE TO RELATED APPLICATIONS

This application is a continuation of U.S. Ser. No. 11/428,090, filed Jun. 30, 2006, now U.S. Pat. No. 7,828,715, entitled "METHOD OF TREATING ANAL INCONTINENCE," which in turn claims priority to provisional application serial number 60/806,209 entitled "Method of Treating Anal Incontinence," which was filed on Jun. 29, 2006, both applications of which are hereby incorporated by reference in their entireties.

BACKGROUND

Mild anal incontinence, which may present as flatal incontinence and/or fecal incontinence, often results from sphincter muscle damage associated with childbirth and/or deterioration of the sphincter muscle with age. Patients exhibiting mild anal incontinence also often present with pelvic organ prolapse, particularly posterior vaginal wall prolapse, with may result in a descent of the rectum into the vagina, referred to as a "rectocele".

One surgical method of treating mild anal incontinence is to dissect and identify the external anal sphincter muscle, and then to bundle and repair the muscle with end-to-end muscle fibre alignment or "waistcoating" overlap of muscle fibres. These procedures, however, are relatively invasive and involve significant tissue dissection. Post-operative pain and hospital stays are also associated with this procedure.

SUMMARY OF THE INVENTION

In one embodiment, the present invention provides a method of treating anal incontinence by forming a tissue pathway extending about a patient's anal sphincter, and implanting an elongate flexible support member in the pathway and extending about the anal sphincter.

In another embodiment, the method includes the steps of forming left and right buttock incisions in locations posterior to the anus and a vaginal incision, and forming a tissue pathway extending between each incision and passing through the perineum. This may be accomplished by passing a surgical needle between the left buttock incision and the vaginal incision, and between the right buttock incision and the vaginal incision.

In a further embodiment, the support member is passed through the pathway using a surgical instrument. For example, the surgical instrument is passed through one buttock incision to the vaginal incision, is associated with one end of the support member, and the support member is passed from the vaginal incision to the buttock incision (or vice-versa). The other end of the support member is passed to the other buttock incision in the same manner. The support member may also be tensioned to provide the desired support are the anal sphincter, and may be sutured to various tissues if desired.

DETAILED DESCRIPTION OF THE PREFERRED EMBODIMENTS

Figure 1:
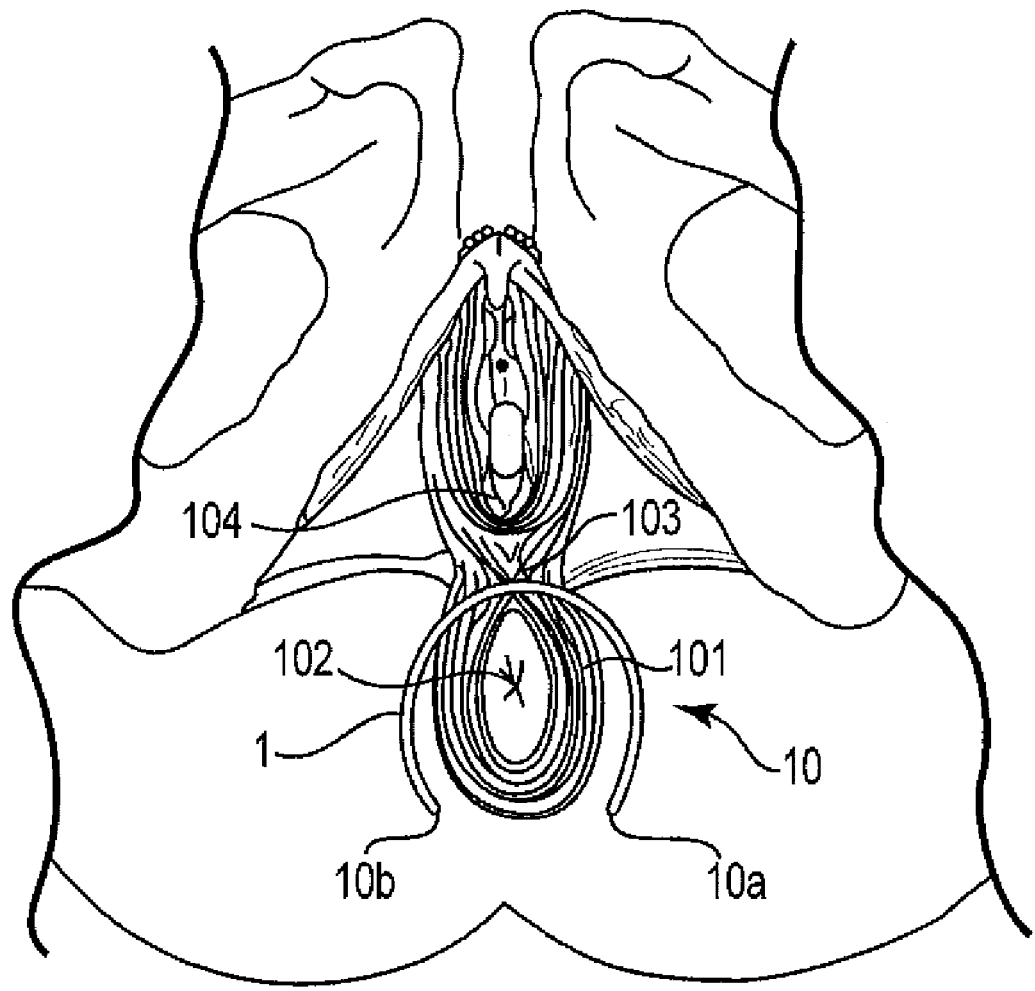
FIG. 1 is a schematic view of the rectogenital area of a patient with an implanted support member.
Figure 2:
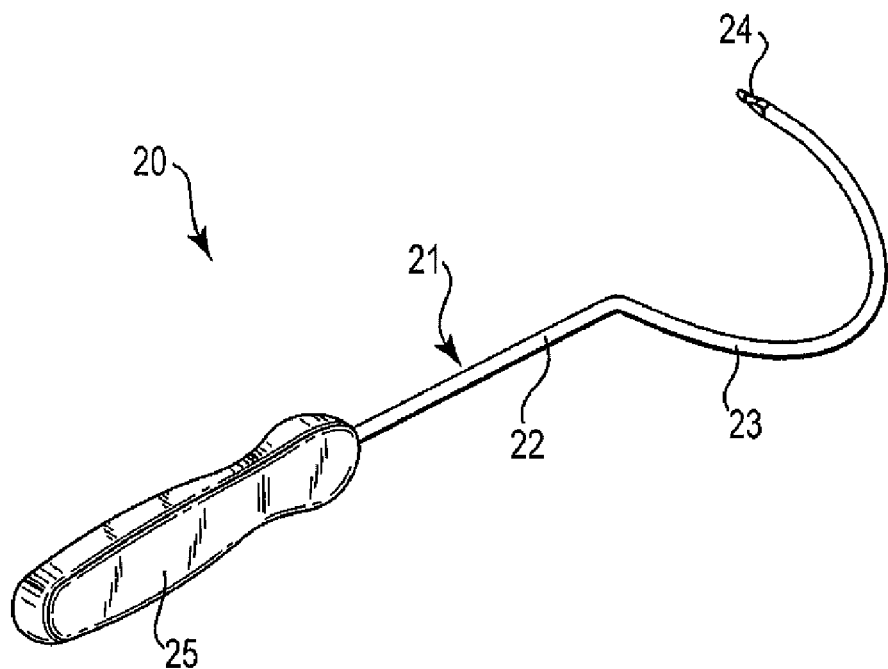
FIG. 2 is a perspective view of a surgical instrument suitable for use to implant the support member shown in FIG. 1.
Figure 3:
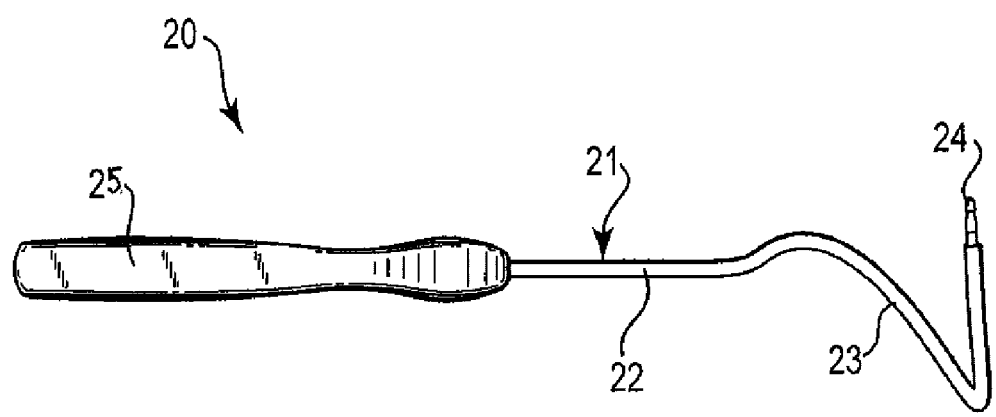
FIG. 3 is a plan view of the surgical instrument of FIG. 2.
Figure 4:
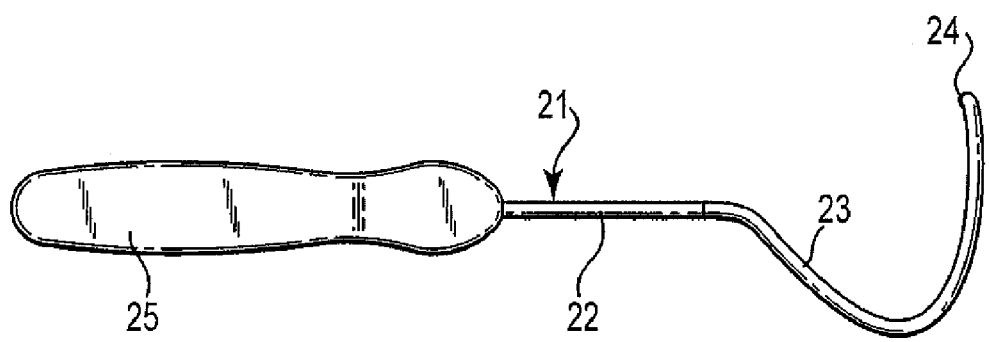
FIG. 4 is a front view of the surgical instrument of FIG. 2.
Figure 5:
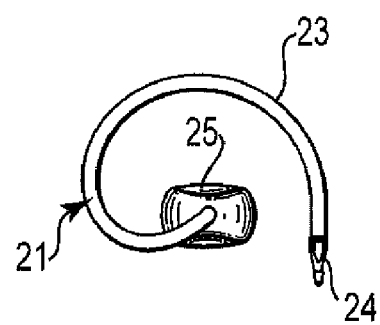
FIG. 5 is an end view of the surgical instrument of FIG. 2.

Referring to FIG. 1, the structure of the rectogenital region of a female patient is schematically depicted with an elongate, flexible, support member 1 in place. The support member 1 is located in and extends along a tissue pathway 10 that has been established in tissue of the patient so as to extend about the anal sphincter 101, which circumferentially envelops the anal passage extending from the anus 102. The support member 1 is located in a supporting relationship with the anal sphincter 101, so as to provide support for the anal sphincter 101, typically the external anal sphincter, in patients suffering from mild anal incontinence.

In the configuration depicted in FIG. 1, the support member 1 extends along the entire length of the tissue pathway 10 about the anal sphincter 101 through an included angle of about 300°, as measured about an axis extending centrally and perpendicularly through the anus 102. The support member 1 extends approximately between the 7 o'clock and 5 o'clock positions of a clockface when viewing the patient in a modified dorsal lithotomy position, as depicted in FIG. 1. Although the illustrated support member 1 extends through an included angle of about 300°, lesser or greater included angles about the anal sphincter 101 are envisaged. In one embodiment, the support member 1 extends through an included angle of at least 180°, and more particularly at least 270°, so as to provide support around a significant portion of the circumference of the anal sphincter 101. Embodiments are also envisaged where the support member 1 extends a full 360° about the circumference of the anal sphincter 101.

In the configuration depicted in FIG. 1, the tissue pathway 10 extends from a left pathway end 10a lateral and posterior to the anus, through the perineum 103 (located between the anterior side of the anal sphincter 101 and the posterior vaginal wall 104) and to a right pathway end 10b located contralateral (i.e., on the patient's right side) and posterior to the anus 102.

Other configurations extending about the anal sphincter 101 are also envisaged, including an effectively reverse configuration extending from a left pathway end lateral and anterior to the anus, through a region posterior to the anus, to a right pathway end contralateral and anterior to the anus 102. Such a pathway might, for example, extend between the 1 o'clock and 11 o'clock positions. Rather than extending along the lateral and contralateral sides of the anal sphincter 101, the tissue pathway 10 might alternatively extend from two pathway ends on the same lateral side of the anus 102, passing posterior and anterior to the anal sphincter 101, to a central pathway region on the contralateral side of the anus 102. The general configuration depicted in FIG. 1 may be the most effective for anal sphincter injuries resulting from childbirth or episiotomy because such injuries generally occur between the 10 o'clock and 2 o'clock positions.

The surgical procedure to support the anal sphincter 101 may be carried out using any of various known support sling systems, including slings used for pubovaginal procedures for stabilising and/or supporting the bladder neck or urethra. Examples of such slings and sling procedures are disclosed in, for example, U.S. Pat. Nos. 5,112,344; 5,611,515; 5,842,478; 5,860,425; 5,899,909; 6,309,686; 6,042,534 and 6,110,101 each of which is incorporated by reference. A variety of slings are also commercially available from American Medical Systems, Inc. of Minnetonka, Minn.

A particularly suitable sling system is disclosed in U.S. Pat. No. 6,911,003, the entire contents of which are hereby expressly incorporated by reference. A commercial embodiment of this system is available from American Medical Systems as the Monarc™ subfascial hammock, and is indicated for the treatment of stress urinary incontinence. The Monarc™ system includes a pair of elongate surgical guide instruments each including a helically formed needle element attached to a handle, an elongate flexible support member (referred to as a support sling) and dilator/connectors for attaching the ends of the support sling to a tip portion of each needle element. Any of various other known sling systems may, however, also be suitable for use with the present pelvic support procedure.

FIGS. 2 to 5 depict an elongate surgical guide instrument 20 disclosed in U.S. Pat. No. 6,911,003 and used in the Monarc™ system. The surgical guide instrument 20 is particularly suitable for use on the left side of the patient's body. A surgical instrument suitable for use on the right side of the patient's body is configured as a mirror image to the surgical instrument 20, with the helical portion extending from the shaft portion in an opposing helix to that of the surgical instrument 20 designed for left side use. The surgical guide instrument 20 includes a needle element 21 having a proximal straight shaft portion 22 fixed to a plastic 25. A distal helical portion 23 of the needle element 21 extends from the shaft portion 22 in a generally helical configuration to a tip portion 24. Although the surgical instrument 20 of the Monarc™ system is configured to pass between an incision adjacent the anterior side of the pubic bone through the obturator foramen to the posterior side of the pubic bone and to emerge from a vaginal incision, the helical shape is also suitable for the present procedure. Many other configurations of surgical instruments, however, are also envisaged, including, for example, C-shaped needles and other curved needle configurations. The specific configuration of the surgical guide instrument is dependent on a number of factors, including the surgeon's preference and varying anatomical sizes of patients. Any configuration of surgical guide element that enables creation of the necessary tissue pathway 10 for placement of the support member 1 will suffice.

The needle portion 21 is typically formed of a durable, biocompatible material such as, but not limited to, stainless steel, titanium, Nitinol various polymers, and combinations of such materials. The needle portion 21 is relatively slender and may have a circular cross-sectional shape having a diameter of less than 3.5 mm to allow for relatively easy passage of the needle portion 21 through tissue so as to establish the tissue pathway 10.

Figure 6:
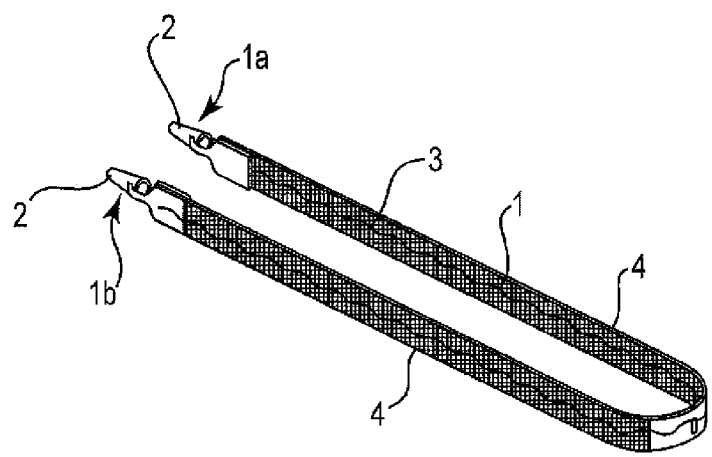
FIG. 6 is a perspective view of a support member according to one embodiment of the present invention.

FIG. 6 depicts an example of a support member 1 suitable for use with the present procedure in the form of a support sling 1 of the Monarc™ system as disclosed in U.S. Pat. No. 6,911,003. The illustrated support sling 1 is a tape formed from a flexible mesh material. The support sling 1 may be formed as a single monolithic piece, or a composite of different components and/or different materials. Suitable synthetic materials for forming the support sling 1 include polymers and metallic materials and, in the case of the Monarc™ sling mesh, polypropylene. The support sling may alternatively be formed of non-synthetic material. Various suitable synthetic and non-synthetic materials are disclosed in U.S. Pat. No. 6,911,003 and additional suitable materials are known in the art. In one embodiment the sling material is elastically deformable. The support sling 1 may also incorporate a coating, such as an anti-bacterial coating, to, for example, fight bacterial infection or reduce the chance of sling rejection by the body. The support sling 1 may have a generally elongate rectangular shape, as depicted, or another elongate shape including, for example, an elongate shape having a broader central region. The Monarc™ system support sling has an unstressed width of approximately 11 mm and length of approximately 350 mm.

The support member 1 is provided with a dilator/connector 2 at each of its first and second ends 1a, 1b. As described in U.S. Pat. No. 6,911,003, the dilator/connector 2 has an open end with internal surfaces adapted to engage corresponding external surfaces on the tip portion 24 of the surgical instrument 20, allowing the support sling 1 to be readily connected to, and extend between, two surgical instruments 20. The external surface of each dilator/connector 2 tapers toward its free end. This taper acts to dilate the tissue pathway 10 as it passes therethrough, providing for ease of passage of the support sling 1. Various other forms of dilator and/or connector may, however, be utilised as desired.

A tensioning suture 3 is woven along the length of the mesh material forming the support sling 1, to assist in tensioning and precise placement of the support sling 1, as will be further described below.

The support sling 1 is encased in two protective sheaths 4, extending from the first and second ends 1a, 1b of the support sling 1 respectively, and overlapping in a central region of the support sling 1. The sheaths 4, which are again further described in U.S. Pat. No. 6,911,003, are typically formed of plastic material, such as polyethylene.

Figure 7:
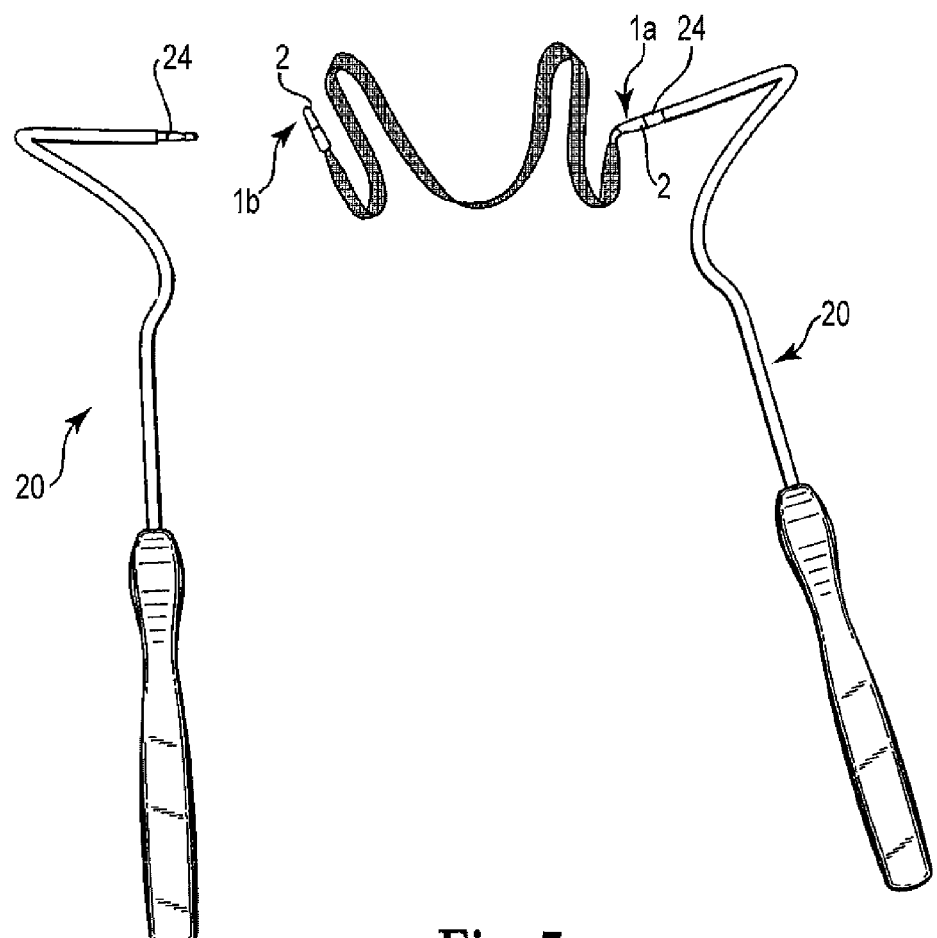
FIG. 7 is a perspective view of a surgical kit including left and right elongate surgical instruments as shown in FIG. 2 and a pelvic support member as shown in FIG. 6.

FIG. 7 depicts a surgical kit including a left surgical guide instrument 20, right surgical guide instrument 20' and support sling 1. The support sling 1 is connected to the tip portion 24 of the left surgical guide instrument 20 by the dilator/connector 2. The sheaths 4 act to protect the support sling 1 during the surgical procedure, and assist in passage of the mesh material of the support sling 1 through the tissue pathway 10.

Figure 8:
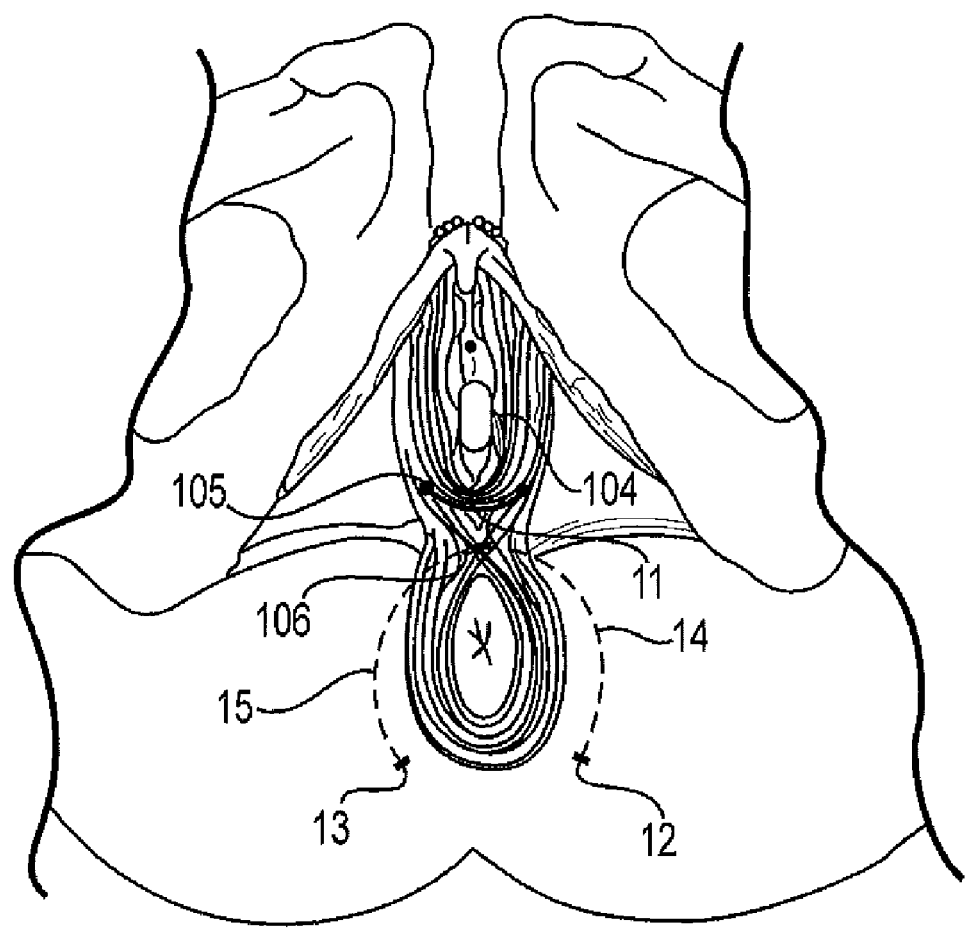
FIG. 8 is a schematic view of the rectogenital area of a patient depicting a perineal incision and left and right buttock incisions.

Suitable implantation procedures can be carried out under local or general anesthesia. The patient should be placed in a modified dorsal lithotomy position with hips flexed, legs elevated in stirrups, and buttocks even with the edge of the able. Vaginal retraction using a weighted vaginal retractor or other means may be utilized if desired. As shown in FIG. 8, the tissue pathway 10 for location of the support sling 1 is established by first making three incisions, a vaginal incision 11, a left buttock incision 12 and a right buttock incision 13.

Vaginal incision 11 extends into the perineum 103, and will typically be a transverse incision of approximately 40-50 mm in length, and may be made in the posterior vaginal wall 104 at or adjacent the posterior vaginal vestibule/hymen ridge 105. The posterior vaginal wall 104 may be further dissected superior and inferior from the vaginal incision 11 so as to expose the perineal body 106 (the central tendon of the perineum 103). Alternatively, an incision could be made directly into the perineum 103 in a location posterior to the vaginal wall 104.

Figure 9:
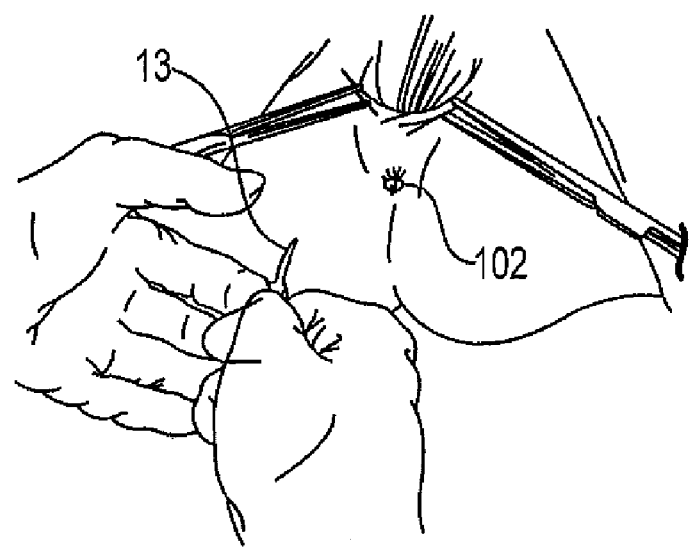
FIG. 9 is a perspective view of the rectogenital area of a patient depicting the creation of a right buttock incision.

Referring to FIGS. 8 and 9, a right buttock incision 13 of approximately 3 mm in length is made at a position corresponding to the right pathway end 10b, lateral and posterior to the anus 102, in the right buttock. The right buttock incision 13 may be made approximately 3 cm lateral to the anus 102 and 3-4 cm posterior. This position is approximately at the 7 o'clock position when viewing the patient in the modified dorsal lithotomy position. A left buttock incision 12 is made in the corresponding position on the contralateral side, corresponding to the left pathway end 10a. The precise location of the left and right buttock incisions 12, 13 may vary according to surgeon preference.

Figure 10:
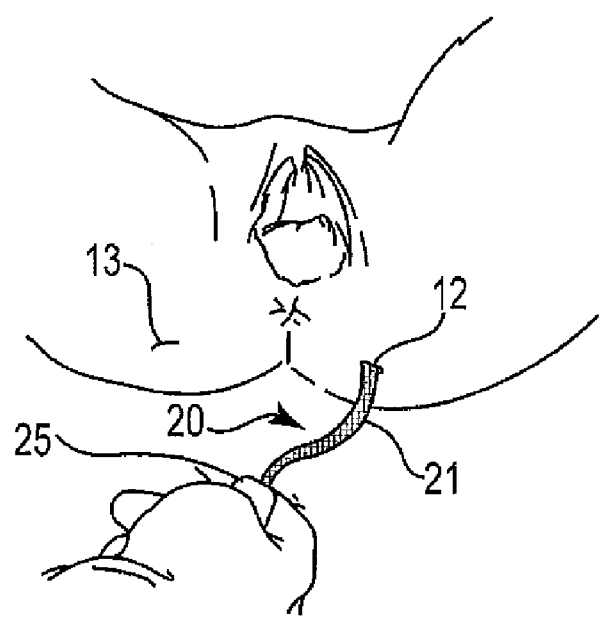
FIG. 10 is a perspective view of the rectogenital region of FIG. 9 depicting the insertion of a surgical guide instrument into a left buttock incision.

A left passage 14 of the tissue pathway 10 is established between the left buttock incision 12 and the vaginal incision 11, using the left surgical instrument 20. The left surgical instrument 20 is inserted into the left buttock incision 12 with the needle tip portion 24 leading, gripping the handle 25 with the right hand. Referring to FIG. 10, the left surgical instrument 20 is oriented such that the needle tip portion 24 is oriented generally perpendicular to the skin at the left buttock incision 12.

Figure 11:
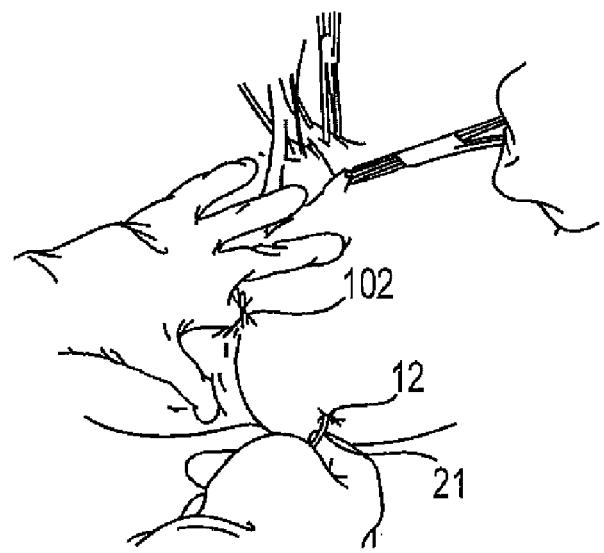
FIG. 11 is a perspective view of the rectogenital region of FIG. 9 depicting further insertion of the surgical guide instrument.

Referring to FIG. 11, the needle tip portion 24 is pushed deeper into the left buttock incision 12, puncturing the initial layers of tissue including the ischiorectal fossa and/or the perianal tissue adjacent to the ischiorectal fossa. The needle tip portion 24 should be advanced in this direction, a distance of approximately 2-3 cm. Whilst the needle tip portion 24 is being advanced, the surgeon's left index finger should be inserted into the patient's anal canal, primarily as a protective mechanism, to ensure that the needle tip portion 24 does not puncture the anal canal. The finger can also serve as a guide, palpating the location of the needle tip portion 24 as it advances.

The left surgical instrument 20 is then rotated, utilizing the helical configuration of the needle element 21 to direct the needle tip portion 24 towards the outside lateral edge of the perineal body 106 and superior to the perineal body 106. The needle tip portion 24 is advanced until it is displayed in the opening created by the vaginal incision 11 and dissected. As the left surgical instrument 20 is advanced to this position, the left index finger may be used to gently pull the anal canal away from the advancing needle element 21, thereby further ensuring integrity of the anal canal is maintained.

The right surgical instrument 20' is taken by the surgeon and the right passage 15 of the tissue pathway 10 is established by the same procedure as discussed above, guiding the needle tip portion 24' of the right surgical instrument 20' through the right buttock incision 13 to the vaginal incision 11, with the surgeon's right index finger inserted in the anal canal.

The support sling 1 is then connected to the left and right surgical instruments 20, 20' by snapping the dilator/connectors 2 at each end 1a, 1b of the surgical sling 1 onto the needle tip portions 24, 24' of the left and right surgical instruments 20, 20' respectively. At this stage, the protective sheaths 4 are left in place over the support sling 1. Both surgical instruments 20, 20' are then pulled back through the left and right passages 14, 15 respectively, drawing the dilator/connector 2 and ends 1a, 1b of the support sling 1 through the left and right passages 14, 15 and out of the left and right buttock incisions 12, 13. The support sling 1 is thus located extending along the tissue pathway 10 from the left buttock incision 12, through the perineum 103 and out of the right buttock incision 13.

The surgical instruments 20, 20', which are now located entirely on the exterior of the patient's body, are removed from the surgical sling 1 by cutting through the sheaths 4 and surgical sling 1 adjacent the dilator/connectors 2.

Figure 12:
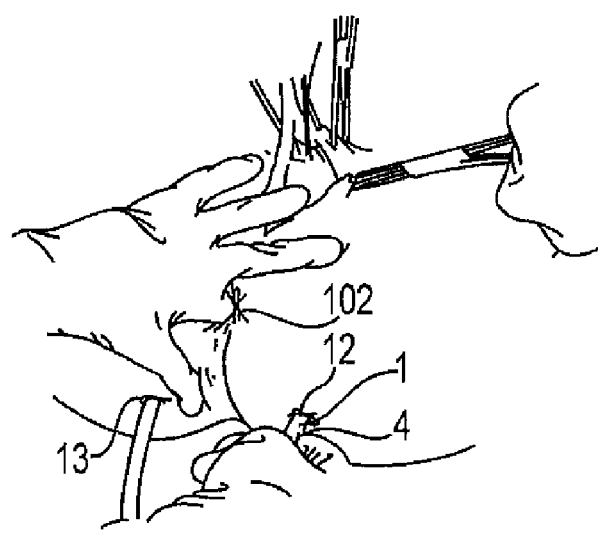
FIG. 12 is a perspective view of the rectogenital region of FIG. 9 depicting a support member extending through both buttock incisions.

Referring to FIG. 12, the surgical sling 1 and overlying protective sheaths 4 are then manually adjusted into the desired position. The support sling 1 should be located sufficiently close to the anal sphincter 101 to provide support, but should not impart any appreciable load on the anal sphincter 101 that would tend to constrict or kink the anal canal.

To draw the surgical sling 1 taut and closer to the periphery of the anal sphincter 101, tension may be applied to each opposing end of the tensioning suture 3 extending along the length of the mesh tape forming the surgical sling 1. With the surgical sling 1 now in the desired position, the protective sheaths 4 may be removed by pulling them through the left and right passages 14, 15 respectively, through the left and right buttock incisions 12, 13.

Once the desired position of the surgical sling has been achieved, the surgical sling 1 may be sutured to the perineal body 106, typically at lateral and contralateral positions, so as to securely fix the surgical sling 1 in the desired position. The sutures may be absorbable, or alternatively may be non-absorbable. The surgical sling 1 is trimmed at the level of the subcutaneous tissue at the let and right buttock incisions 12, 13. The left and right buttock incisions 12, 13 and vaginal incision 11 and dissection are then closed.

Although the above described procedure utilizes an "outside-in" approach to establish the passages 14, 15 of the tissue pathway 10, an "inside-out" approach may alternatively be utilized. In such an approach, a modified form of a surgical guide instrument having a detachable handle, an example of which is again disclosed in U.S. Pat. No. 6,911,003, may be utilized. The needle elements of these alternate surgical instruments are passed from the vaginal incision 11 to the left and right buttock incisions 12, 13 to establish the left and right passages 14, 15 with the handles attached to a first end of the needle element extending through the vaginal incision 11. The handles are then removed from the first end of each of the needle elements, and attached to the opposing second end of the needle elements, which at this stage of the procedure extend through the buttock incisions. The surgical sling is then connected to the first end of the needle elements and drawn through the left and right passages by again drawing the needle elements back through the passages. If desired one passage could be formed by the "outside-in" approach, and the other by the "inside-out" approach.

In a further embodiment, a single passage extending from the left buttock incision 12 to the right buttock incision 13, via the perineum 103, could be formed by utilizing a single needle that extends through the entire pathway. This embodiment would eliminate the need for the perineal incision and/or one of the buttock incisions.

If the surgeon desires to create the tissue pathway with a different configuration (such as, for example, between the 1 o'clock and 11 o'clock positions), alternate incisions may be required to establish the tissue pathway. For example, for a 1 o'clock to 11 o'clock configuration, a first incision would be made anterior and lateral to the anus, a second incision contralateral and anterior to the anus and a third central incision made posterior to the anus between the buttocks. Such a tissue pathway may also be established by a single passage, omitting the need for the central posterior incision.

Given that many patients suffering from mild anal incontinence also experience pelvic organ prolapse, it will often be beneficial to conduct the above described pelvic support procedure together with a procedure to treat the pelvic organ prolapse. A particularly suitable system and treatment for pelvic organ prolapse is described in US Patent Application Publication No. US 2005/0245787 A1, the entire contents of which are hereby expressly incorporated by cross-reference. A commercial embodiment of this system is available from American Medical Systems, Inc. as the Apogee™ Vault Suspension System. The Apogee™ system includes a support sling and surgical guide instrument.

Figure 13:
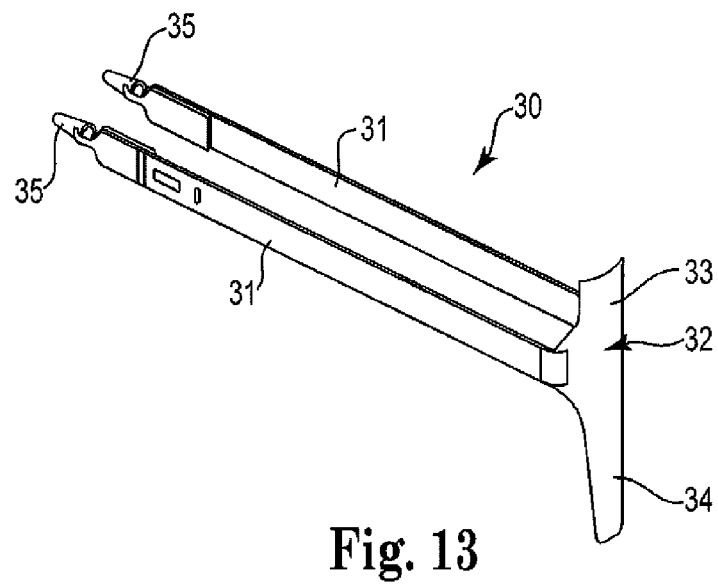
FIG. 13 is a perspective view of an Apogee™ vault suspension member.

An example of an Apogee™ support sling is depicted in FIG. 13. The support sling 30 includes first and second elongate mesh tapes 31 supporting a central support element 32, commonly referred to as a cape, which extends above and below the points of attachment of the mesh tapes 31, to form a superior cape flap 33 and an inferior cape flap 34. The cape 32 is formed of a mesh material, similar to the mesh tapes 31. Versions of the Apogee™ system are also available without the cape 32, with the support sling being in the form of a continuos mesh tape, and a further version is available utilizing what is referred to as bio-cape. The free ends 31a of the mesh tapes 31 are provided with dilator/connectors 35 for attachment to a surgical needle.

Figure 14:
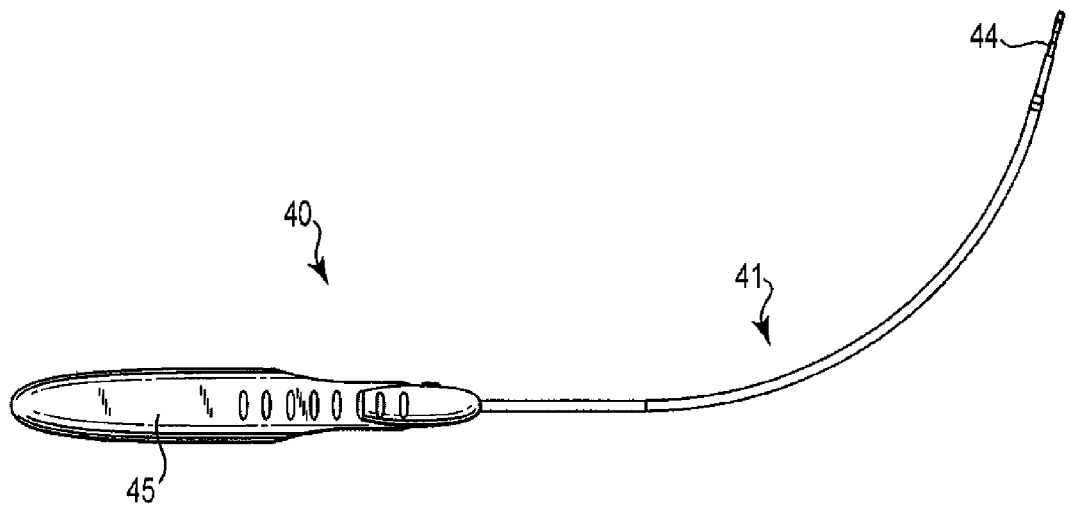
FIG. 14 is a front elevation view of an Apogee™ surgical guide instrument.

Referring to FIG. 14, a surgical guide instrument 40 of the Apogee™ system includes a curved needle element 41 and a handle 45. A tip portion 44 of the needle element 41 has a cooperating connector structure for engaging the dilator/connectors 35 of the sling support 30. Although this Apogee™ system is particularly suitable for treating pelvic organ prolapse, other pelvic organ prolapse repair systems may be utilized as desired.

When carrying out a pelvic organ prolapse treatment such as the Apogee™ procedure in combination with the previously described anal support procedure, the procedure is carried out with certain modifications.

Figure 15:
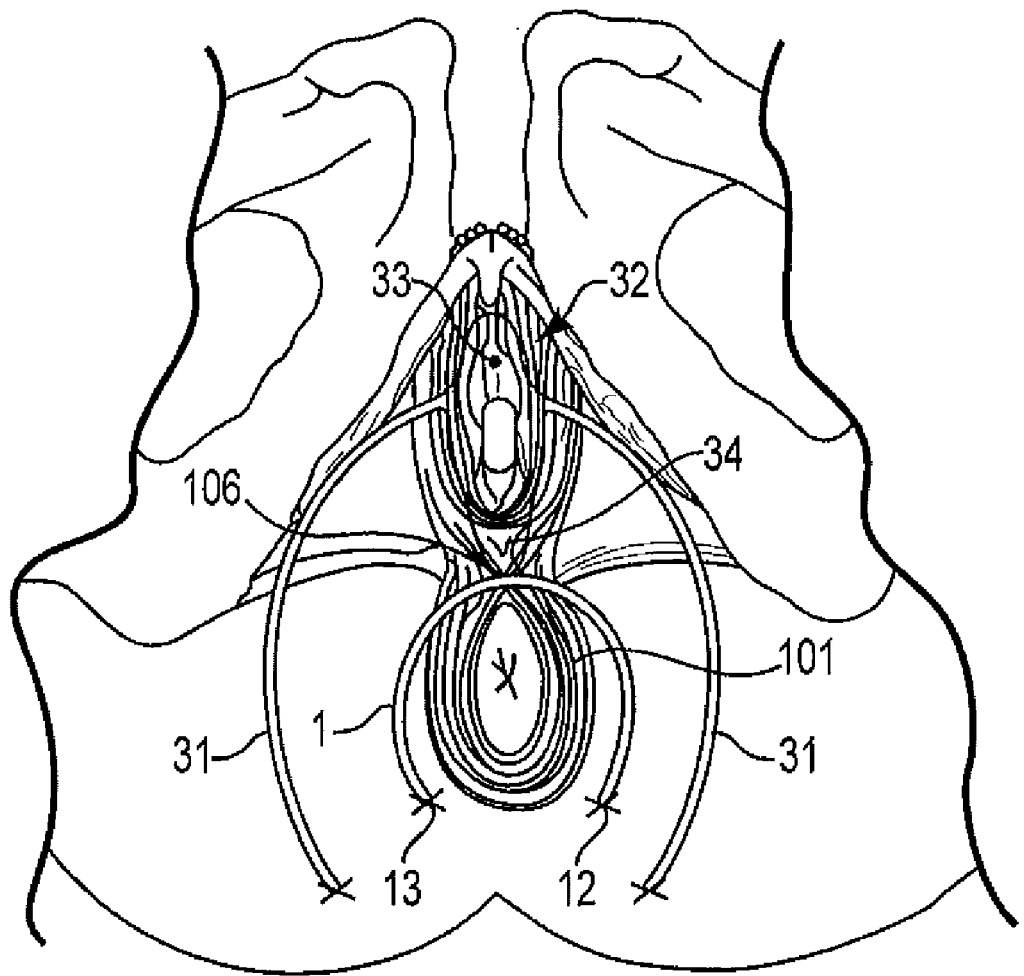
FIG. 15 is a schematic view of a rectogenital region with an implanted support member and an implanted Apogee™ vault suspension member.

First, the buttock incisions for establishing the tissue pathway for implanting the Apogee™ support sling, which would normally be adjacent to or above the buttock incisions for the anal support procedure, are made further lateral and posterior, as indicated in FIG. 15. For example, the left and right buttock incisions 52, 53 for the Apogee™ procedure may be located approximately 2 cm lateral and 3-4 cm posterior to the left and right buttock incisions 12, 13 formed for the pelvic support procedure. The surgical guide instrument 40 is then used to establish the left and right passages of the tissue pathway for the Apogee™ procedure following the same general path as described in US Patent Application Publication No. 2005/0245787 A1, in front of the ischial spine, through the levator muscle and to the incision and dissection to the posterior vaginal incision and dissection created for placement of the cape. This tissue pathway extends lateral and superior to the tissue pathway 10 of the present pelvic support procedure. The vaginal dissection for placing the cape will extend from the initial vaginal incision for the Apogee™ process (located superior to the vaginal incision 11), down to the vaginal incision 11. As the inferior flap 34 of the cape 32 of the Apogee™ support sling 30 typically extends down to a position adjacent the perineal body 106, the inferior flap 34 may be sutured to the perineal body 106 with the same lateral and contralateral suturing performed during the pelvic support procedure to secure the pelvic support sling 1 to the perineal body 106. This may improve the fixation of the Apogee™ cape 32, which would otherwise be relatively loosely located within the soft tissue of the posterior vaginal wall.

The person skilled in the art will appreciate that the above described procedures may be varied as desired by the surgeon, depending on personal preferences, anatomical size of patient, and specific patient symptoms. The above described procedures may also be carried out utilizing a variety surgical support sling kits in addition to the Monarc™ and/or Apogee™ systems referred to above. The pelvic support procedure could also be carried out on male patients suffering from mild anal incontinence, and both male and female patients suffering from urge fecal incontinence.

The invention claimed is:

1. A method of treating anal incontinence in a patient comprising:
    establishing a pathway in tissue of the patient extending about the anal sphincter, wherein said pathway extends from a left pathway end laterally left and posterior to the anus, through the perineum, to a right pathway end laterally right and posterior to the anus, and wherein the step of establishing said pathway comprises:
    making a left buttock incision in the patient's left buttock at said left pathway end;
    making a right buttock incision in the patient's right buttock at said right pathway end;
    making an incision in the posterior vaginal wall that extends into the perineum;
    establishing a left passage of said pathway extending between said left buttock incision and said vaginal incision; and
    establishing a right passage of said pathway extending between said right buttock incision and said vaginal incision;
    implanting an elongate flexible support member in and extending along said pathway to support the anal sphincter,
    wherein the elongate flexible support member comprises a central portion and exactly two elongate extension portions extending from the central portion.

2. The method of claim 1, wherein:
    the step of establishing said left passage comprises passing an elongate surgical instrument between said left buttock incision and said vaginal incision; and
    the step of establishing said right passage comprises passing an elongate surgical instrument between said right buttock incision and said vaginal incision.

3. The method of claim 2, wherein the step of locating said support member comprises:
    securing a first end of said support member to an elongate surgical instrument;
    drawing said elongate surgical instrument and said first end of said support member through said left passage; and
    securing a second end of said support member to an elongate surgical instrument; and
    drawing said elongate surgical instrument and said second end of said support member through said right passage.

4. The method of claim 1 further comprising the step of suturing said support member to the perineal body.

5. A method of treating anal incontinence in a patient comprising:
    forming a first incision in the buttock of the patient posterior to the anus;
    forming a second incision in the opposite buttock posterior to the anus;
    forming a tissue pathway between the first and second incisions by passing a surgical instrument between the first incision and the perineum anterior to the anus, and between the second incision and the perineum anterior to the anus; and implanting a support member in the tissue pathway such that the support member is positioned around a substantial portion of the circumference of the anal sphincter, wherein the support member comprises a central portion and exactly two elongate extension portions extending from the central portion.

6. The method of claim 5 comprising forming a vaginal incision in the posterior vaginal wall, wherein the tissue pathway is formed by passing the surgical instrument from the first incision to the vaginal incision and from the second incision to the vaginal incision.

7. The method of claim 5 wherein said support member extends about the anal sphincter through an included angle of at least about 180°, measured about an axis extending centrally and perpendicularly through the anus.

8. The method of claim 5 comprising placing the support member in a supporting relationship with the anal sphincter to provide support for the external anal sphincter.

9. The method of claim 5 comprising placing a finger in the patient's anal canal and palpating a tip of the elongate surgical instrument.

10. The method of claim 5 comprising adjusting the support member with tension to draw the support member to a periphery of the anal sphincter.

11. The method of claim 5 wherein the support member comprises a mesh sling consisting of an elongate mesh strip.

12. The method of claim 11 wherein the support member comprises a connector at a distal end.

13. The method of claim 11 wherein the support member comprises a protective sheath.

* * * * *

UNITED STATES PATENT AND TRADEMARK OFFICE
CERTIFICATE OF CORRECTION

PATENT NO. : 8,371,998 B2
APPLICATION NO. : 12/891941
DATED : February 12, 2013
INVENTOR(S) : Maxwell E. Haverfield It is certified that error appears in the above-identified patent and that said Letters Patent is hereby corrected as shown below:

In the Specifications

Column 4, line 65, "able" should be -- table --.

Column 6, line 33, "let" should be -- left --.

Signed and Sealed this
Seventh Day of May, 2013

Teresa Stanek Rea
*Acting Director of the United States Patent and Trademark Office*